United States Patent
Akashi et al.

(10) Patent No.: US 9,214,638 B2
(45) Date of Patent: Dec. 15, 2015

(54) MATERIAL FOR ORGANIC ELECTROLUMINESCENT DEVICE AND ORGANIC ELECTROLUMINESCENCE DEVICE INCLUDING THE SAME

(71) Applicants: SAMSUNG DISPLAY CO., LTD., Yongin, Gyeonggi-Do (KR); NATIONAL UNIVERSITY CORPORATION HOKKAIDO UNIVERSITY, Sapporo-shi, Hokkaido (JP)

(72) Inventors: Nobutaka Akashi, Yokohama (JP); Masako Kato, Sapporo (JP); Hiroki Ohara, Sapporo (JP); Atsushi Kobayashi, Sapporo (JP)

(73) Assignees: SAMSUNG DISPLAY CO., LTD., Yongin, Gyeonggi-Do (KR); NATIONAL UNIVERSITY CORPORATION HOKKAIDO UNIVERSITY, Sapporo-shi, Hokkaido (JP)

(*) Notice: Subject to any disclaimer, the term of this patent is extended or adjusted under 35 U.S.C. 154(b) by 0 days.

(21) Appl. No.: 14/668,225

(22) Filed: Mar. 25, 2015

(65) Prior Publication Data
US 2015/0280148 A1    Oct. 1, 2015

(30) Foreign Application Priority Data
Mar. 26, 2014    (JP) .................... 2014-064085

(51) Int. Cl.
C07F 1/08    (2006.01)
H01L 51/50    (2006.01)
H01L 51/00    (2006.01)

(52) U.S. Cl.
CPC ............. *H01L 51/0091* (2013.01); *C07F 1/08* (2013.01); *H01L 51/5012* (2013.01)

(58) Field of Classification Search
USPC .......................... 313/504; 428/690; 546/10, 2
See application file for complete search history.

(56) References Cited

U.S. PATENT DOCUMENTS 7,875,366 B2    1/2011    Tsuboyama et al.

FOREIGN PATENT DOCUMENTS

JP    2012-106995    6/2012
WO    WO 2015/018322    *    2/2015 ............. G01N 21/64

OTHER PUBLICATIONS

Faqian, L. et al.: A new copper (I) complex based on imidazole and triphenylphosphine ligands: Synthesis, structure, third-order NLO, and fluorescence properties. Chin. J. Chem., vol. 30, pp. 1069-1074, 2012.*
Anders Lennartson, (3-acetylpyridine-kappa N)chlorobis(triphenylphosphine-kappa P) copper(I): a suitable candidate for absolute asymmetric synthesis?, ActaCrystallographica, Jul. 2006, vol. 62, pp. 1569-1571.
Lutz M. Engelhardt, Lewis-base adducts of Group 11 metal(I) compounds, LI, Synthesis and structural characterization of monomuclear chloro-,bromo- and iodopyridinebis(triphenylphosphine)copper(I) complexes, Australian Journal of Chemistry, 1989, vol. 42, pp. 895-905.
Jens Hagen, Carbonylation of 1-decene with modified copper(I) complex catalysts, Chemiker-Zeitung, 1985, vol. 109, pp. 3-9.
W.T. Reichle, Preparation, physical properties, and reactions of copper(I)-triphenyl-M complexes (M=phosphorus, arsenic, antimony, InorganicaChimicaActa, 1971, vol. 5(3), pp. 325-332.
Hiroki Ohara, et al. Highly Luminescent Mononuclear Copper(I)-Halide Complexes, Dept. of Chemistry, Faculty of Science, Hokkaido University, 20th International Symposium on the Photophysics and Photochemistry of Coordination Compounds, Jul. 7-11, 2013, Traverse City, Michigan, USA.
Najma Sultana, et al. Copper(I) Complexes of Triphenylphosphine and 2-methylpyridine, Pak. J. Sci. Ind. Res. vol. 40, Nos. 5-12, May-Dec. 1997.
D. Saravanabharathi, et al. Is Copper(I) really soft? Probing the hardness of Cu(I) with pyridinecarboxaldehyde ligands, Proc. Indian Acad. Sci, Chemi. Sci., vol. 114, No. 4, Aug. 2002, pp. 347-356.
Jian-Bao Li et al. Crystal Structure of bis(triphenylphospine-kP)(bromo-kBr)-(isoqunnoline-kN)copper(I), CuBr(PC 1 8H15)2(i-C9H7N), Z. Kristallogr. NCS 226 (2011 109-111/ DOI 10.1524/ncrs. 2011.0051.
Najima Sultana et al. Synthesis and Characterization of Cu(I) complexes of triphenylphosphine and 2-methylpyridine, Indian Journal of Chemistry., vol. 33A, Jan. 1994, pp. 63-65.

* cited by examiner

*Primary Examiner* — Charanjit Aulakh
(74) *Attorney, Agent, or Firm* — Lee & Morse, P.C.

(57) ABSTRACT

A material for an organic electroluminescent (EL) device includes a copper(I) complex represented by the following Formula 1:

[CuX(PPh$_3$)$_2$L]    [Formula 1]

In the above Formula 1, X is an anion, PPh$_3$ is triphenylphosphine, and L is a substituted or unsubstituted heterocyclic ligand having 5 to 18 ring carbon.

12 Claims, 10 Drawing Sheets

MATERIAL FOR ORGANIC ELECTROLUMINESCENT DEVICE AND ORGANIC ELECTROLUMINESCENCE DEVICE INCLUDING THE SAME

CROSS-REFERENCE TO RELATED APPLICATION

Japanese Patent Application No. 2014-064085, filed on Mar. 26, 2014, in the Korean Intellectual Property Office, and entitled: "Material For Organic Electroluminescent Device and Organic Electroluminescence Device Including The Same," is incorporated by reference herein in its entirety.

BACKGROUND

1. Field

Embodiments relate to a material for an organic electroluminescent device and an organic electroluminescent device including the same.

2. Description of the Related Art

An organic electroluminescence diode, which is a self-emitting type device, is being actively developed. The organic electroluminescent device (hereinafter referred to as an organic EL device) embodies light emission of a luminescent material including an organic compound of an emission layer by recombining holes and electrons injected from an anode and a cathode into the emission layer.

An example of an organic EL device includes an emission layer and another layer stacked on the emission layer, such as a hole transport layer and an electron transport layer for transporting holes or electrons as carrier to the emission layer. In addition, to improve the emission efficiency of the organic EL device, various compounds are examined as materials used in the organic EL device.

In addition, various compounds have been synthesized recently without limiting to organic EL device field. For example, a method of synthesizing a copper(I) complex including triphenylphosphine and 2-methylpyridine as a ligand has been disclosed, and the copper(I) complex thus synthesized is known to be colored lightly.

SUMMARY

Embodiments are directed to a material for an organic electroluminescent (EL) device, the material comprising a copper(I) complex represented by the following Formula 1:

[CuX(PPh$_3$)$_2$L]  [Formula 1]

In the above Formula 1, X is an anion, PPh$_3$ is triphenylphosphine, and L is a substituted or unsubstituted heterocyclic ligand having 5 to 18 ring carbon.

The copper(I) complex may exhibit delayed fluorescence.

The heterocyclic ligand may be a nitrogen-containing heterocyclic ligand.

The nitrogen-containing heterocyclic ligand may be represented by one of the following ligands (2) to (22):

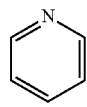

(2)

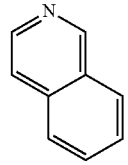

(3)

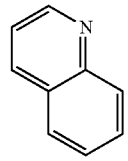

(4)

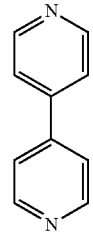

(5)

(6)

(7)

(8)

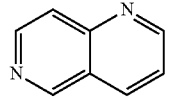

(9)

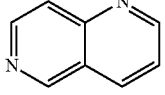

(10)

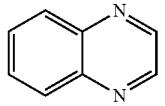

(11)

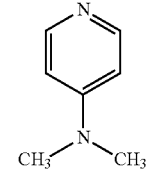

(12)

(13) 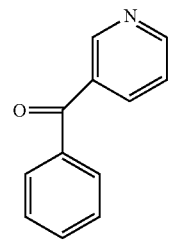

(14) 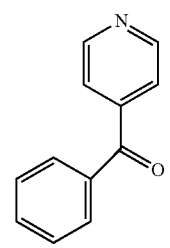

(15) 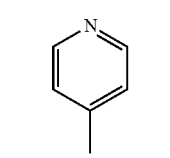

(16) 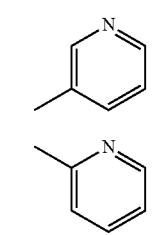

(17) 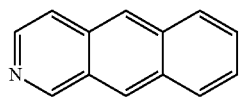

(18) 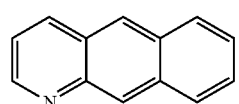

(19) 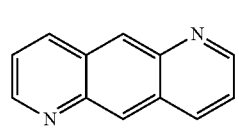

(20) 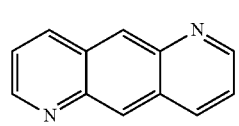

(21) 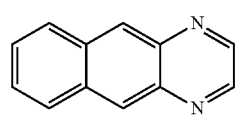

(22)

The nitrogen-containing heterocyclic ligand is one of 4-methylpyridine, i-quinoline, and 1,6-naphthyridine.

X may be an anion selected from the group of a halide ion, a nitrate ion, and a perchlorate ion.

X may be one of $Cl^-$, $Br^-$ and $I^-$.

The copper(I) complex may be a compound represented by one of the following Formulae (1A) to (1C):

Formula (1A)

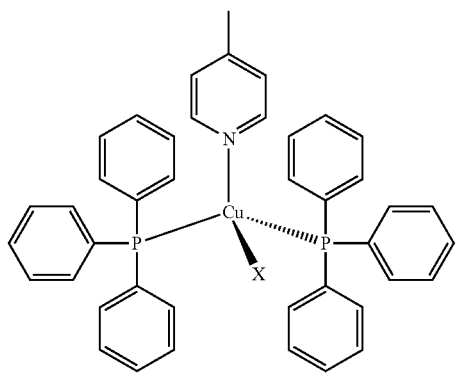

Formula (1B)

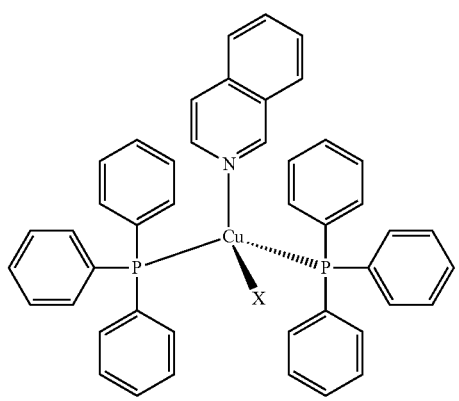

Formula (1C)

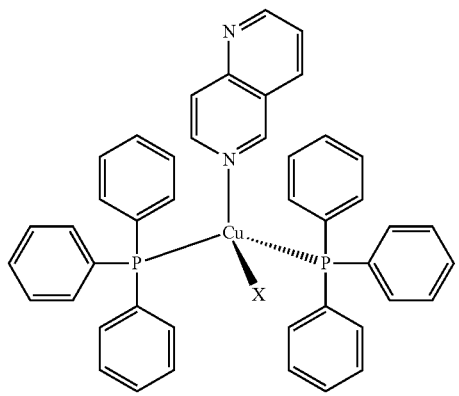

In the above Formulae (1A) to (1C), X is one of $Cl^-$, $Br^-$ and $I^-$.

Embodiments are also directed to an organic electroluminescent (EL) device, including a copper(I) complex represented by the following Formula 1:

$$[CuX(PPh_3)_2L]$$  [Formula 1]

In the above Formula 1, X is an anion, PPh₃ is triphenylphosphine, and L is a substituted or unsubstituted heterocyclic ligand having 5 to 18 ring carbon atoms.

The copper(I) complex may exhibit delayed fluorescence.

The heterocyclic ligand may be a nitrogen-containing heterocyclic ligand.

The nitrogen-containing heterocyclic ligand may be represented by one of the following ligands (2) to (22):

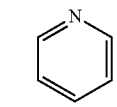
(2)

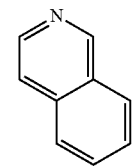
(3)

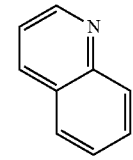
(4)

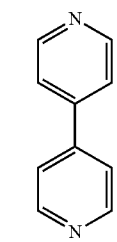
(5)

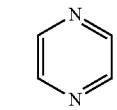
(6)

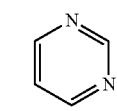
(7)

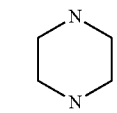
(8)

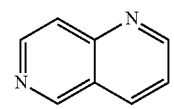
(9)

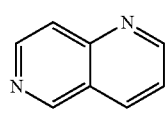
(10)

-continued

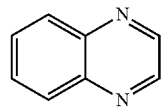
(11)

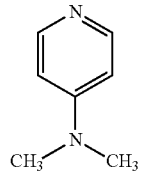
(12)

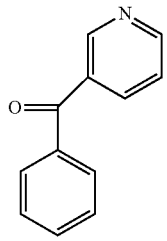
(13)

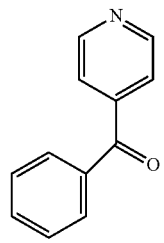
(14)

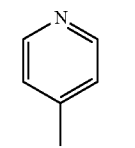
(15)

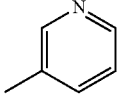
(16)

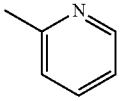
(17)

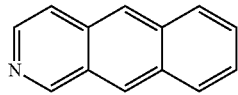
(18)

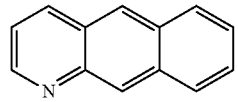
(19)

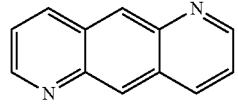
(20)

(21)

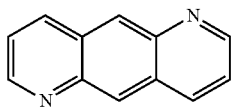

(22)

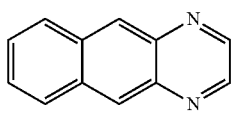

The nitrogen-containing heterocyclic ligand may be one of 4-methylpyridine, i-quinoline, and 1,6-naphthyridine.

X may be an anion selected from the group of a halide ion, a nitrate ion, and a perchlorate ion.

X may be one of Cl$^-$, Br$^-$ and I$^-$.

The copper(I) complex may be a compound represented by one of the following Formulae (1A) to (1C):

Formula (1A)

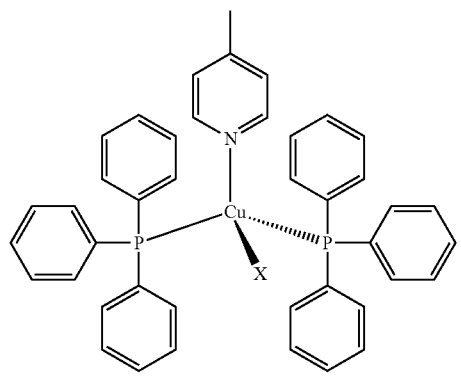

Formula (1B)

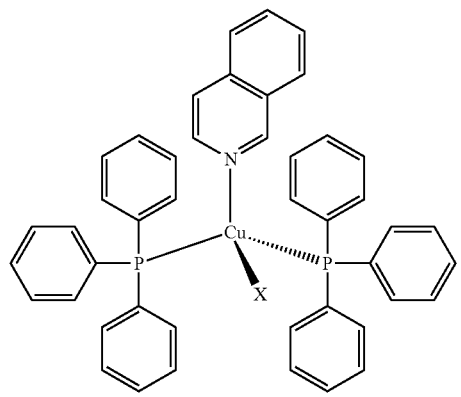

Formula (1C)

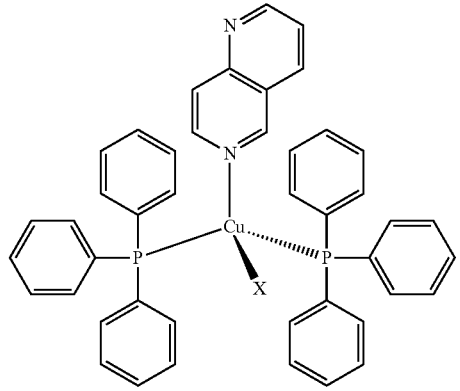

In the above Formulae (1A) to (1C), X is one of Cl$^-$, Br$^-$ and I$^-$.

BRIEF DESCRIPTION OF THE DRAWINGS

Features will become apparent to those of skill in the art by describing in detail exemplary embodiments with reference to the attached drawings in which.

DETAILED DESCRIPTION

Figure 1:
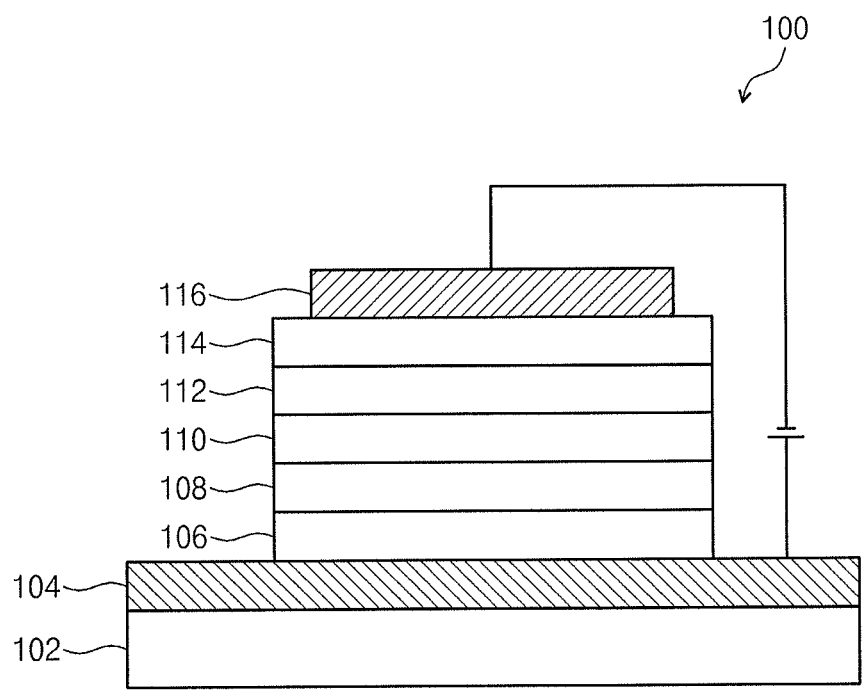
FIG. 1 illustrates a schematic diagram depicting an organic EL device according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. In addition, it will also be understood that when a layer is referred to as being "between" two layers, it can be the only layer between the two layers, or one or more intervening layers may also be present.

Luminescent Material for Organic EL Device

First, a luminescent material for an organic EL device according to an embodiment will be explained.

The luminescent material for an organic EL device according to an embodiment includes a copper(I) complex represented by the following Formula 1.

[CuX(PPh$_3$)$_2$L]  [Formula 1]

In the above Formula 1, X is an anion, PPh$_3$ is triphenylphosphine and L is a substituted or unsubstituted heterocyclic ligand having 5 to 18 ring carbon atoms.

As discussed in more detail below, it is believed that the copper(I) complex represented by the above Formula 1 exhibits delayed fluorescence.

The term "delayed fluorescence" refers to a light emitting phenomenon via a process other than known fluorescence or phosphorescence as the light emitting principle of the organic EL device. The delayed fluorescence is described in detail referring to FIG. 6. Subpart (a) of FIG. 6 provides an illustration explaining the light emitting process of fluorescence and phosphorescence, and subpart (b) of FIG. 6 provides an illustration explaining the light emitting process of delayed fluorescence.

In general, when holes and electrons injected respectively from an anode and a cathode recombine in an emission layer to produce excitons in an organic EL device, about 35% of excitons having a singlet excited state (S$_1$) and about 65% of excitons having a triplet excited state (T$_1$) are generated. As shown in subpart (a) of FIG. 6, fluorescence is the light emitting phenomenon generated during transition 330 from the singlet excited state (S$_1$) 310a to a ground state (S$_0$) 300, and the phosphorescence is light emitting phenomenon generated during transition 340 from the triplet excited state (T$_1$) 320a to the ground state (S$_0$) 300.

For example, when a fluorescent material is used as the luminescent material of the organic EL device, only about 25% of the excitons of the singlet excited state (S$_1$) 310a may be used for light emission, and about 75% of the excitons of the triplet excited state (T$_1$) 320a may be deactivated as heat and not used for the light emission. In addition, when a phosphorescent material is used as the luminescent material for the organic EL device, about 75% of the excitons of the triplet excited state (T$_1$) 320a may be used. However, a phosphorescent material typically includes a rare earth metal such as iridium (Ir) or platinum (Pt) which are expensive.

Figure 6:
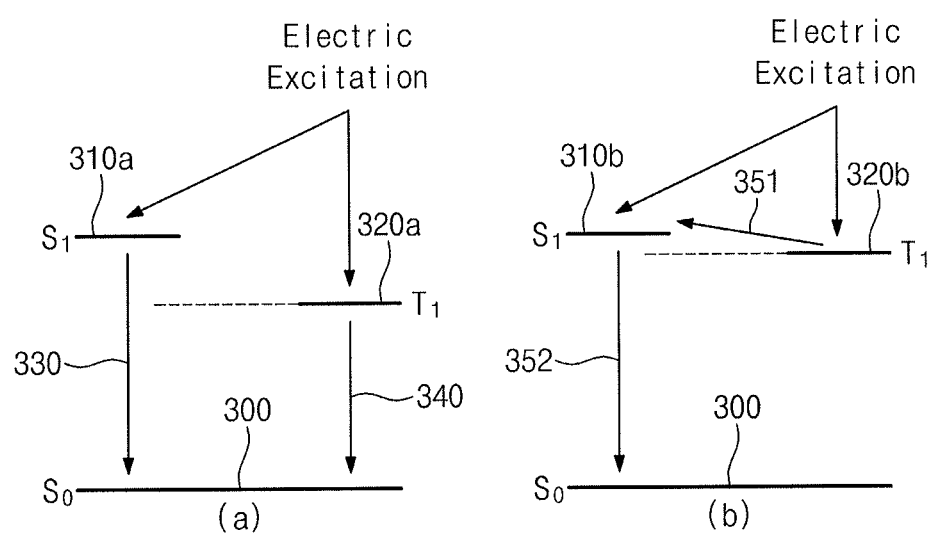
FIG. 6 illustrates an explanation of delayed fluorescence.

As illustrated in subpart (b) of FIG. 6, delayed fluorescence is generated when the energy difference between the singlet excited state (S$_1$) 310b and the triplet excited state (T$_1$) 320b is extremely small. Delayed fluorescence is a light emitting phenomenon generated when a reverse energy transition 351 from the triplet excited state (T$_1$) 320b to the singlet excited state (S$_1$) 310b is generated by the absorption of thermal energy, etc., and then, transition 353 from the singlet excited state (S$_1$) 310b to the ground state (S$_0$) 300 is generated. In addition, when the energy is reversely transitioned from the triplet excited state (T$_1$) 320b to the singlet excited state (S$_1$) 310b, the lifetime of the light thus generated may be longer than that of light generated by fluorescence or phosphorescence. This light is differentiated from common fluorescence. Accordingly, the light emitting phenomenon is referred to as delayed fluorescence.

When a luminescent material that exhibits delayed fluorescence is used as the luminescent material of the organic EL device, about 25% of the excitons of the singlet excited state (S$_1$) 310b may emit fluorescence normally. In addition, about 75% of the excitons of the triplet excited state (T$_1$) 320b may reversely transition to the singlet excited state (S$_1$) 310b by the absorption of the thermal energy, thereby emitting fluorescence. Therefore, when the luminescent material exhibiting delayed fluorescence is used as the luminescent material of the organic EL device, all excitons may be used for light emission, and emission efficiency may be largely improved with respect to a general fluorescent material and a general phosphorescent material.

The luminescent material for an organic EL device according to an embodiment includes a copper(I) complex represented by the above Formula 1, which is found to exhibit delayed fluorescence. Thus, the luminescent material for an organic EL device according to an embodiment may realize further higher emission efficiency when compared to the luminescent material for an organic EL device including a general fluorescent material and a general phosphorescent material. The luminescent material for an organic EL device according to an embodiment may be an inexpensive copper complex. An organic EL device may be manufactured with a lower cost when compared to using a general phosphorescent material that includes a rare earth metal.

Here, the structure of the copper(I) complex represented by the above Formula 1 and included in the luminescent material for an organic EL device according to an embodiment will be explained in more detail.

In the above Formula 1, L is a substituted or unsubstituted heterocyclic ligand having 5 to 18 ring carbon atoms. For example, L may be a substituted or unsubstituted nitrogen-containing heterocyclic ligand having 5 to 18 ring carbon atoms. According to this configuration, L may form a coordinate bond with a central metal, copper, by the lone pair electron of nitrogen included in a heterocycle.

For example, L may be a nitrogen-containing cyclic compound represented by one of the following ligands (2) to (22). The following nitrogen-containing heterocyclic ligands may form a coordinate bond with a central metal, copper, by the lone pair electron of nitrogen included in the heterocycle. The nitrogen-containing cyclic ligand represented by one of the following ligands (2) to (22) may have an advantage that no steric hindrance may be generated with other ligands such as triphenylphosphine (PPh$_3$), etc.

(2)

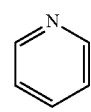

(3) 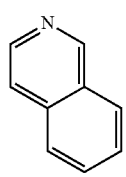
(4) 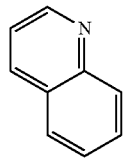
(5) 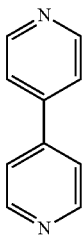
(6) 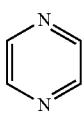
(7) 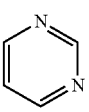
(8) 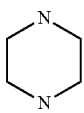
(9) 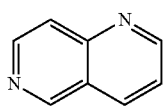
(10) 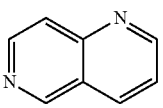
(11) 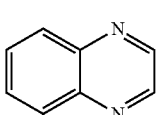
(12) 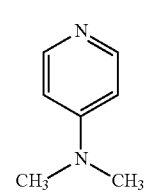
(13) 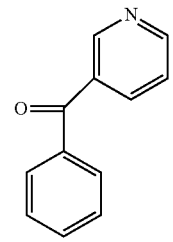
(14) 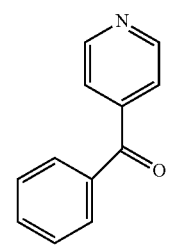
(15) 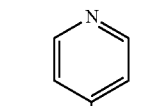
(16) 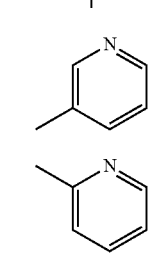
(17) 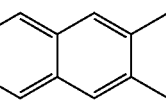
(18) 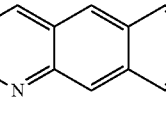
(19) 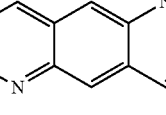
(20) 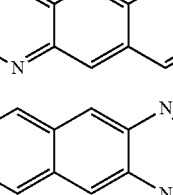
(21)
(22)
For example, L may be one of 4-methylpyridine, i-quinoline and 1,6-naphthyridine. For example, L may be 1,6-naphthyridine.
When L is the 1,6-naphthyridine, the emitting color of the copper (I) complex may be red. In addition, by changing ligand X, the wavelength of light and quantum yield may be changed. For example, when L is 1,6-naphthyridine, the wavelength of the light may be controlled according to the organic EL device used. On the other hand, when L is i-quinoline, the light emitting process of the excitons of the triplet excited state ($T_1$) may become mainly phosphorescence rather than delayed fluorescence.

In the above Formula 1, X is an anion. For example, X may be an anion selected from the group of a halide ion, a nitrate ion and a perchlorate ion. For example, X may be one of $Cl^-$, $Br^-$ and $I^-$.

Particular examples of the copper(I) complex represented by the above Formula 1 include one compound represented in the following Formulae (1 A) to (1 C).

Formula (1A)

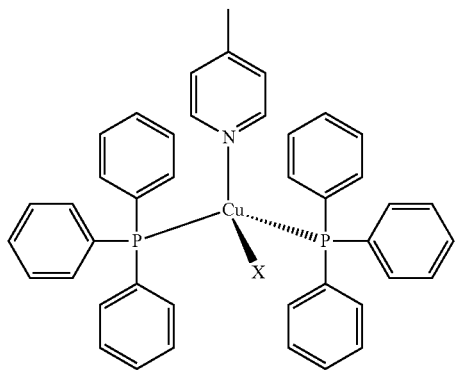

Formula (1B)

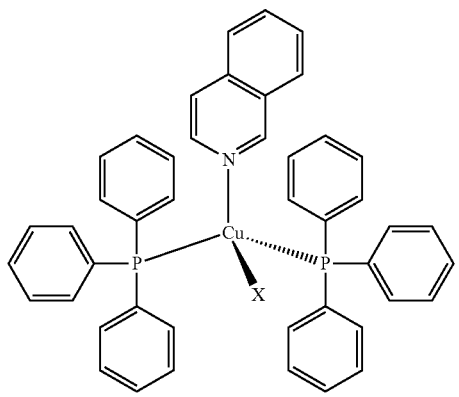

Formula (1C)

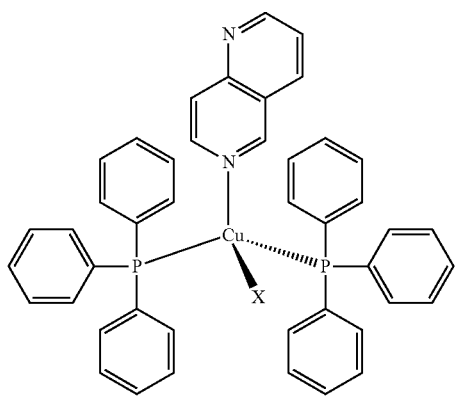

In the above Formulae (1A) to (1C), X may be one of $Cl^-$, $Br^-$ and $I^-$.

The copper(I) complex represented by the above-described Formula 1 may exhibit delayed fluorescence as verified in the following examples. Thus, the luminescent material for an organic EL device including the copper(I) complex represented by the above Formula 1 may improve the emission efficiency of the organic EL device.

Structure of Organic EL Device

Referring to FIG. 1, an organic EL device using the luminescent material for an organic EL device according to an embodiment will be explained. FIG. 1 is a schematic diagram illustrating an embodiment of an organic EL device according to an embodiment.

As shown in FIG. 1, an organic EL device 100 according to an embodiment may include a substrate 102, an anode 104 disposed on the substrate 102, a hole injection layer 106 disposed on the anode 104, a hole transport layer 108 disposed on the hole injection layer 106, an emission layer 110 disposed on the hole transport layer 108, an electron transport layer 112 disposed on the emission layer 110, an electron injection layer 114 disposed on the electron transport layer 112 and a cathode disposed on the electron injection layer 114. In some implementations, a portion of the layers of the organic EL device 100 may be omitted, and other layers may be added. In some implementations, one or more layers of the organic EL device 100 may be formed as a multilayer.

The substrate 102 may be, for example, a transparent glass substrate, a semiconductor substrate formed using silicon (Si), etc., a flexible substrate made of a resin, etc.

The anode 104 may be disposed on the substrate 102. The anode 104 may be formed using, for example, a metal having high work function, an alloy, a conductive compound, etc. For example, the anode 104 may be formed using indium tin oxide (ITO), indium zinc oxide (IZO), etc.

The hole injection layer 106 may be disposed on the anode 104. The hole injection layer 106 may include, for example, 4,4',4"-tris[2-naphthyl(phenyl) amino]triphenylamine (2-TNATA), N,N,N',N'-tetrakis(3-methylphenyl)-3,3'-dimethylbenzidine (HMTPD), dipyrazino[2,3-f:2'3'-h]quinoxaline-2,3,6,7,10,11-hexacarbonitrile (HAT(CN)6, poly(3,4-ethylenedioxythiophene)/poly(4-styrenesulfonate) (PEDOT/PSS), etc.

The hole transport layer 108 may be disposed on the hole injection layer 106.

The hole transport layer 108 may include, for example, N,N'-bis(3-methylphenyl)-N,N'-diphenylbenzidine (TPD), 4,4',4"-tris(N-carbazolyl)triphenylamine (TCTA) and N,N'-di(1-naphthyl)-N,N'-diphenylbenzidine (NPD).

The emission layer 110 may be disposed on the hole transport layer 108. The emission layer 110 may include the luminescent material for an organic EL device according to an embodiment. In addition, the emission layer 110 may include, for example, 9,10-di(2-naphthyl)anthracene (ADN), poly(N-vinylcarbazole) (PVCz), etc., as a host material. In addition, the emission layer 110 may include a hole transport material used in the hole transport layer 108, etc. or an electron transport material used in the electron transport layer 112, etc.

The electron transport layer 112 may be disposed on the emission layer 110 The electron transport layer 112 may include, for example, tris(8-hydroxyquinolinato)aluminum (Alq3), 3-(4-biphenylyl)-4-phenyl-5-(4-tert-butylphenyl)-4H-1,2,4-triazole (TAZ), etc.

The electron injection layer 114 may be disposed on the electron transport layer 112. The electron injection layer 114 may include, for example, lithium fluoride (LiF), sodium chloride (NaCl), cesium fluoride (CsF), lithium oxide ($Li_2O$), barium oxide (BaO), etc.

The cathode 116 may be disposed on the electron injection layer 114. the cathode 116 may include, for example, a metal having low work function, an alloy, a conductive compound, etc. For example, the cathode 116 may be formed using a metal such as Al, or a transparent material such as ITO, IZO, etc.

In the structure of the organic EL device 100 shown in FIG. 1, other suitable materials for an organic EL device may be used in, for example, the cathode 104, the hole injection layer 106, the hole transport layer 108, the electron transport layer 112, the electron injection layer 114 and the cathode 116.

Each layer of the organic EL device 100 according to an embodiment may be formed by selecting an appropriate layer forming method, such as a vacuum deposition method, a sputtering method, various coating methods, etc., according to the material used.

For example, electrode layers such as the anode 104 and the cathode 116 may be formed by selecting a deposition method including an electron beam evaporation method, a hot filament evaporation method or a vacuum deposition method, a sputtering method, or a plating method (an electroplating method or an electroless plating method).

An organic layer such as the hole injection layer 106, the hole transport layer 108, the emission layer 110, the electron transport layer 112, the electron injection layer 114, etc. may be formed by a physical vapor deposition (PVD) method, such as a vacuum deposition method, a printing method, such as a screen printing method or an ink jet printing method, a laser transcription method or a coating method, such as a spin coat method.

As described above, an embodiment of the organic EL device 100 according to an embodiment has been explained. The organic EL device according to an embodiment may include the copper(I) complex showing delayed fluorescence in the emission layer 110. Accordingly, emission efficiency may be increased.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

Hereinafter, a copper(I) complex with delayed fluorescence and an organic EL device according to an embodiment will be explained in detail referring to examples and comparative examples Synthesis of Copper(I) Complex with Delayed Fluorescence Copper(I) complexes including a luminescent material for an organic EL device according to embodiments were synthesized by the following synthetic methods, as examples. In addition, the single crystalline X-ray structure of the copper (I) complex thus synthesized was interpreted by using a CCD type single crystalline X-ray diffraction apparatus manufactured by Rigaku Co. (Mercury CCD) and interpretation software (Crystal Structure). The interpretation results of the single crystalline X-ray structure are illustrated in FIGS. 2A to 2I.

Synthetic Example 1

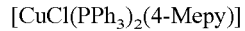
[CuCl(PPh$_3$)$_2$(4-Mepy)]

Figure 2A:
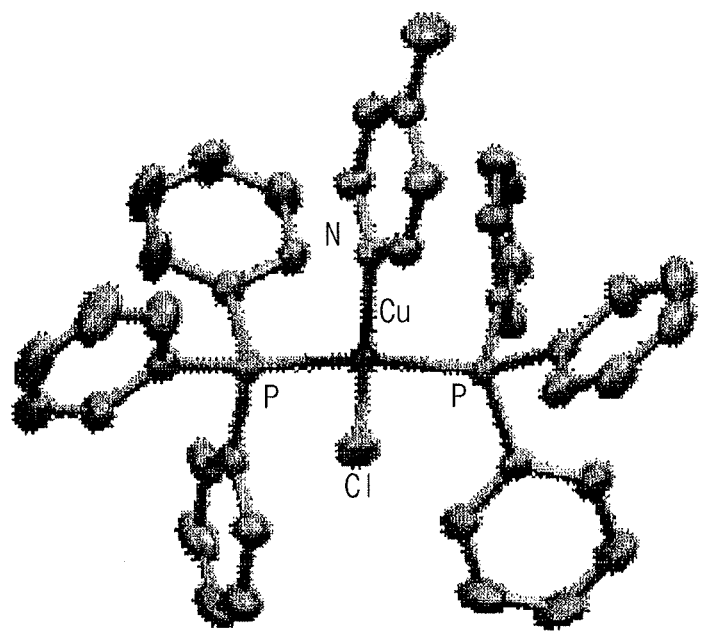
FIG. 2A illustrates a diagram depicting the interpretation result of a single crystalline X-ray structure of a copper(I) complex of Synthetic Example 1.

A solution obtained by adding γ-picoline (1 mL) and CHCl$_3$ (1 mL) to [CuCl(PPh$_3$)$_3$] (88.7 mg, 0.096 mmol) was controlled. The solution thus obtained was recrystallized by a vapor-liquid diffusion method using ether overnight. [CuCl(PPh$_3$)$_2$(4-Mepy)] (39 mg) was produced as a colorless crystal with 56% yield. The interpretation results of the single crystalline X-ray structure of the crystal thus obtained is illustrated in FIG. 2A. Herein, PPh$_3$ represents triphenylphosphine and 4-Mepy represents 4-methylpyridine (ligand (15)).

Synthetic Example 2

Figure 2B:
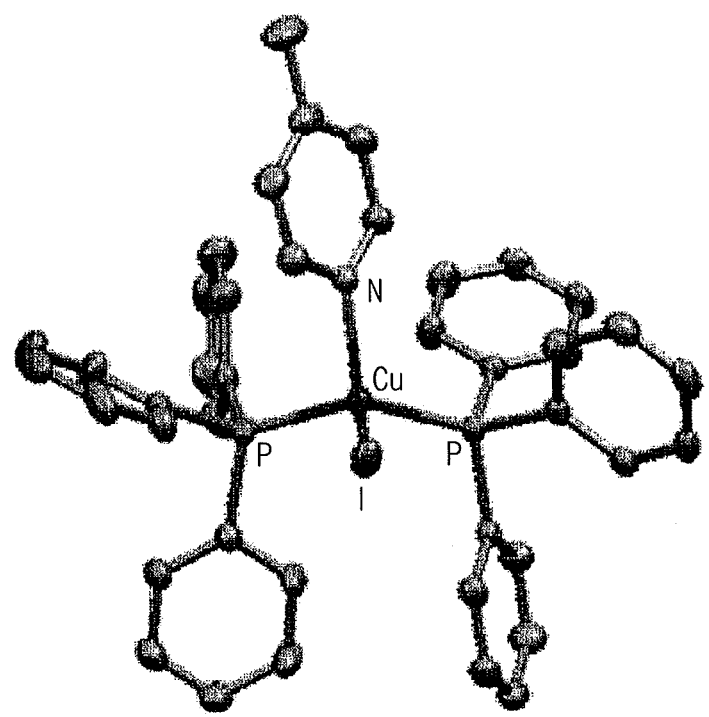
FIG. 2B illustrates a diagram depicting the interpretation result of a single crystalline X-ray structure of a copper(I) complex of Synthetic Example 2.

[CuBr(PPh$_3$)$_2$(4-Mepy)]

γ-Picoline (1 mL) and PPh$_3$ (680 mg, 2.6 mmol) were added to CuBr (42.5 mg, 0.30 mmol). CHCl$_3$ (1 mL) was added thereto. The precipitate thus produced was removed by filtering, and filtrate was recrystallized by a vapor-liquid diffusion method using ether overnight. [CuBr(PPh$_3$)$_2$(4-Mepy)] (110 mg) was produced as a colorless crystal with 47% yield. The interpretation results of the single crystalline X-ray structure of the crystal thus obtained is illustrated in FIG. 2B.

Synthetic Example 3

Figure 2C:
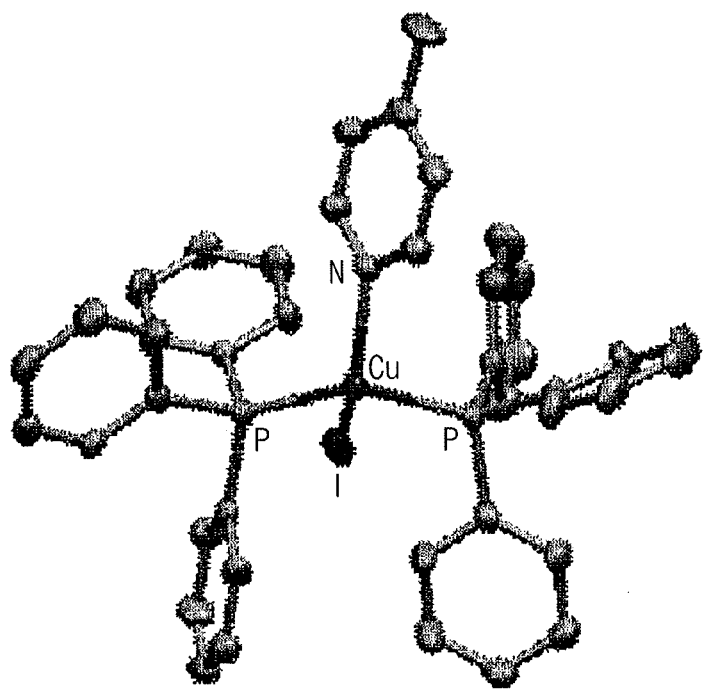
FIG. 2C illustrates a diagram depicting the interpretation result of a single crystalline X-ray structure of a copper(I) complex of Synthetic Example 3.

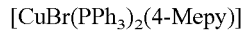
[CuI(PPh$_3$)$_2$(4-Mepy)]

γ-Picoline (1 mL) and PPh$_3$ (660 mg, 2.5 mmol) were added to CuI (48.9 mg, 0.26 mmol). In addition, CHCl$_3$ (1 mL) was added thereto. The solution thus produced was recrystallized by a vapor-liquid diffusion method using ether for two days, and a colorless crystal was precipitated. Diffused liquid was extracted and covered, followed by standing for one week to produce [CuI(PPh$_3$)$_2$(4-Mepy)] (177.1 mg) as a colorless crystal with 85% yield. The interpretation results of the single crystalline X-ray structure of the crystal thus obtained is illustrated in FIG. 2C.

Synthetic Example 4

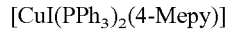
[CuCl(PPh$_3$)$_2$(iq)]

Figure 2D:
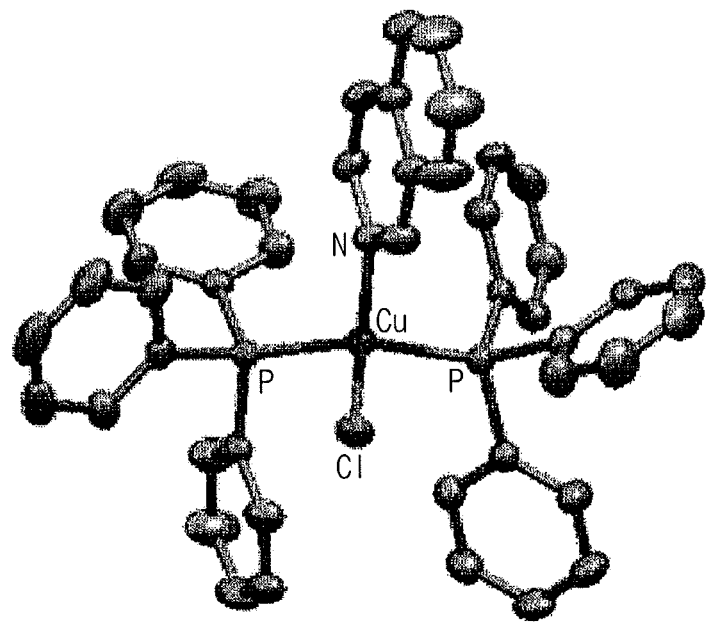
FIG. 2D illustrates a diagram depicting the interpretation result of a single crystalline X-ray structure of a copper(I) complex of Synthetic Example 4.

A solution obtained by adding isoquinoline (1 mL) and CHCl$_3$ (1 mL) to [CuCl(PPh$_3$)$_3$].CH$_3$CN (90.4 mg, 0.098 mmol) was controlled. The solution thus produced was recrystallized by a vapor-liquid diffusion method using ether overnight. [CuCl(PPh$_3$)$_2$(iq)] (43.8 mg) was produced as a yellow crystal with 60% yield. The interpretation results of the single crystalline X-ray structure of the crystal thus obtained is illustrated in FIG. 2D. Herein, iq represents i-quinoline (ligand (3)).

Synthetic Example 5

[CuBr(PPh$_3$)$_2$(iq)]

Figure 2E:
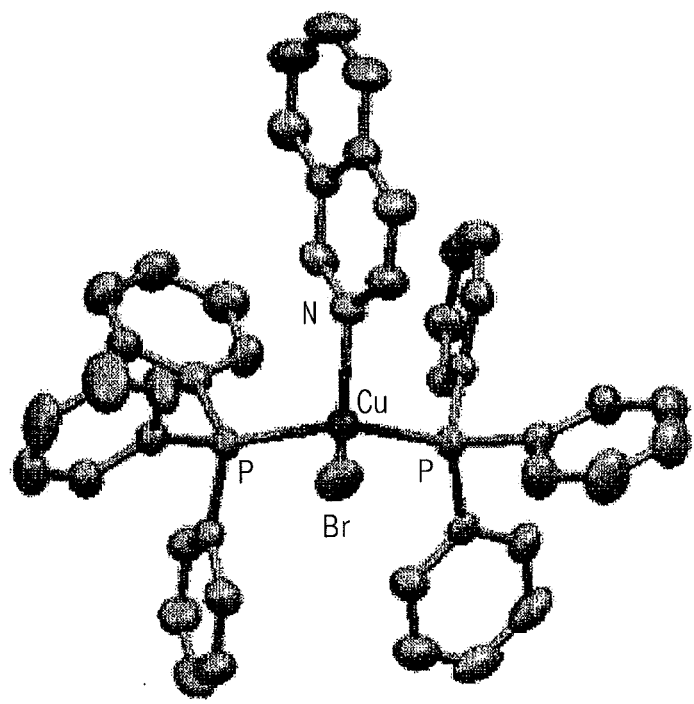
FIG. 2E illustrates a diagram depicting the interpretation result of a single crystalline X-ray structure of a copper(I) complex of Synthetic Example 5.

A solution obtained by adding PPh$_3$ (153.8 mg, 0.59 mmol) and isoquinoline (1 mL) to CuBr (37.5 mg, 0.24 mmol) and diluting using CHCl₃ (2 mL) was controlled. The controlled solution thus obtained was recrystallized by a vapor-liquid diffusion method using ether overnight to produce [CuBr(PPh₃)₂(iq)] (128.7 mg) as a yellow crystal with 69% yield. The interpretation results of the single crystalline X-ray structure of the crystal thus obtained is illustrated in FIG. 2E.

Synthetic Example 6

[CuI(PPh₃)₂(iq)]

Figure 2F:
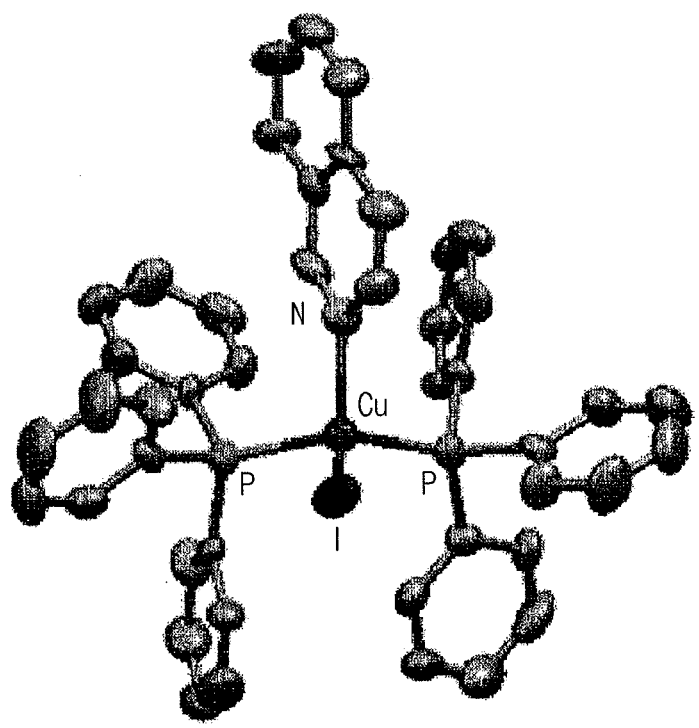
FIG. 2F illustrates a diagram depicting the interpretation result of a single crystalline X-ray structure of a copper(I) complex of Synthetic Example 6.

About 2 eq. of PPh₃ (1.12 mmol) with respect to CuI was added to CuI (52.3 mg, 0.28 mmol) and dissolved in an excessive amount (2-3 mL) of isoquinoline. After the dissolution, the isoquinoline was frozen and hardened in a short time, and so, CHCl₃ was added to dissolve the isoquinoline again. The solution thus obtained was recrystallized by a vapor-liquid diffusion method using ether overnight to produce [CuI(PPh₃)₂(iq)] (210 mg) as a yellow crystal with 89% yield. The interpretation results of the single crystalline X-ray structure of the crystal thus obtained is illustrated in FIG. 2F.

Synthetic Example 7

[CuCl(PPh₃)₂(1,6-nap)]

Figure 2G:
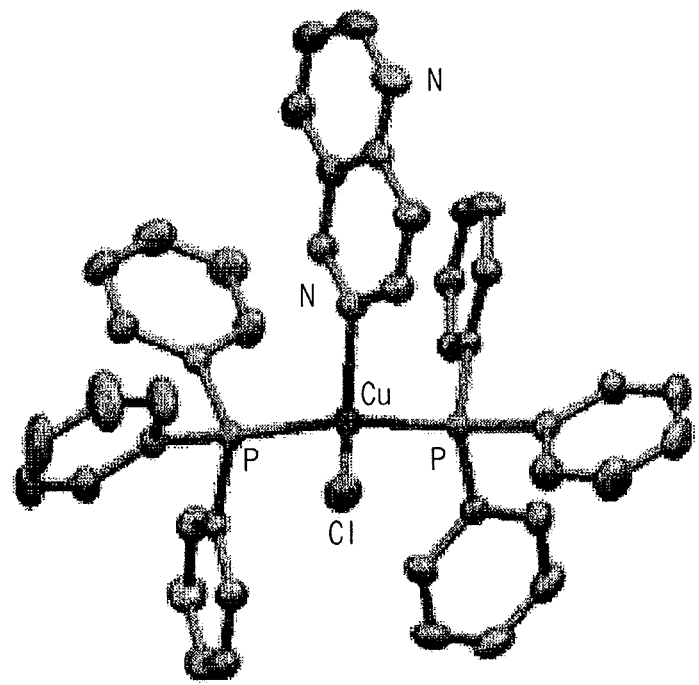
FIG. 2G illustrates a diagram depicting the interpretation result of a single crystalline X-ray structure of a copper(I) complex of Synthetic Example 7.

A solution of 1,6-naphthyridine (100 mg, 0.77 mmol) in CHCl₃ (1 mL) was added to [CuCl(PPh₃)₃]·CH₃CN (49.6 mg, 0.054 mmol). The solution thus obtained was recrystallized by a vapor-liquid diffusion method using ether for three days to produce [CuCl(PPh₃)₂(1,6-nap)] (20.5 mg) as a yellow crystal with 52% yield. The interpretation results of the single crystalline X-ray structure of the crystal thus obtained is illustrated in FIG. 2G. Here, 1,6-nap represents 1,6-naphthyridine (ligand (10)).

Synthetic Example 8

[CuBr(PPh₃)₂(1,6-nap)]

Figure 2H:
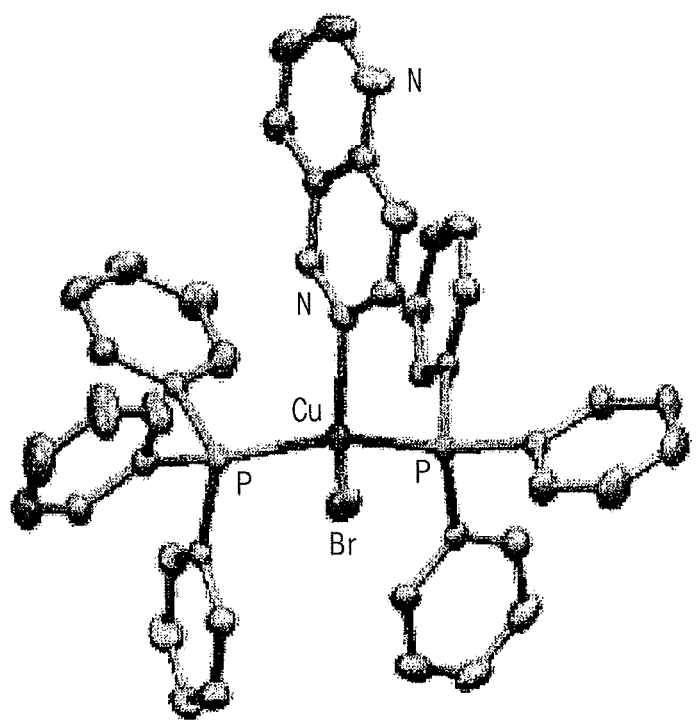
FIG. 2H illustrates a diagram depicting the interpretation result of a single crystalline X-ray structure of a copper(I) complex of Synthetic Example 8.

A solution of 1,6-naphthyridine (100 mg, 0.77 mmol) in CHCl₃ (1 mL) was added to [CuBr(PPh₃)₃] (56.8 mg, 0.061 mmol). The solution thus obtained was recrystallized by a vapor-liquid diffusion method using ether overnight to produce [CuBr(PPh₃)₂(1,6-nap)] (43.1 mg) as a yellow crystal with 89% yield. The interpretation results of the single crystalline X-ray structure of the crystal thus obtained is illustrated in FIG. 2H.

Synthetic Example 9

[CuI(PPh₃)₂(1,6-nap)]

Figure 2I:
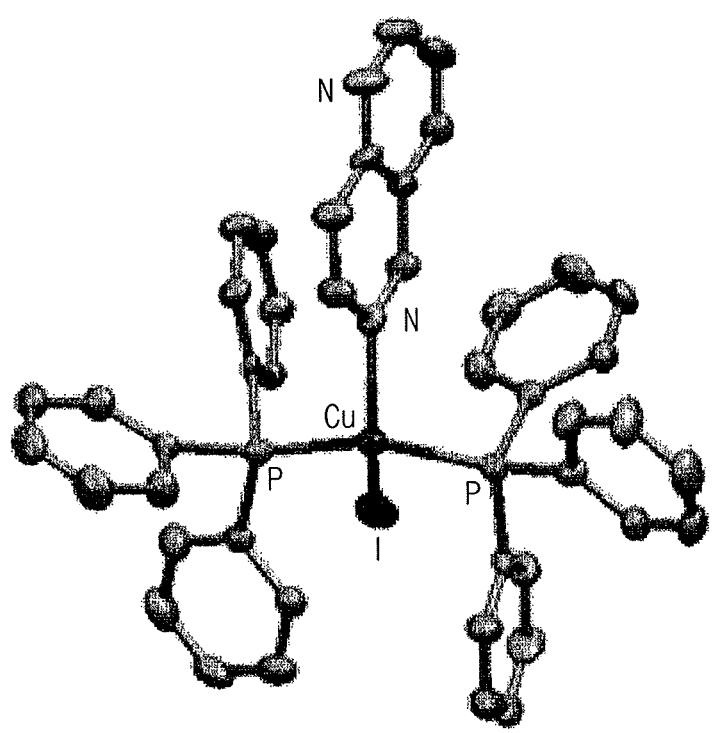
FIG. 2I illustrates a diagram depicting the interpretation result of a single crystalline X-ray structure of a copper(I) complex of Synthetic Example 9.

A solution of 1,6-naphthyridine (101.8 mg, 0.78 mmol) in CHCl₃ (1 mL) was added to [CuI(PPh₃)₃] (63.3 mg, 0.065 mmol). The solution thus obtained was recrystallized by a vapor-liquid diffusion method using ether overnight to produce [CuI(PPh₃)₂(1,6-nap)] (31.1 mg) as a yellow crystal with 57% yield. The interpretation results of the single crystalline X-ray structure of the crystal thus obtained is illustrated in FIG. 2I.

Evaluation of Properties of Copper(I) Complex

Hereinafter, the interpretation results on the emission properties of the copper(I) complexes synthesized above will be shown, and the delayed fluorescence of the copper(I) complex will be explained.

Figure 3:
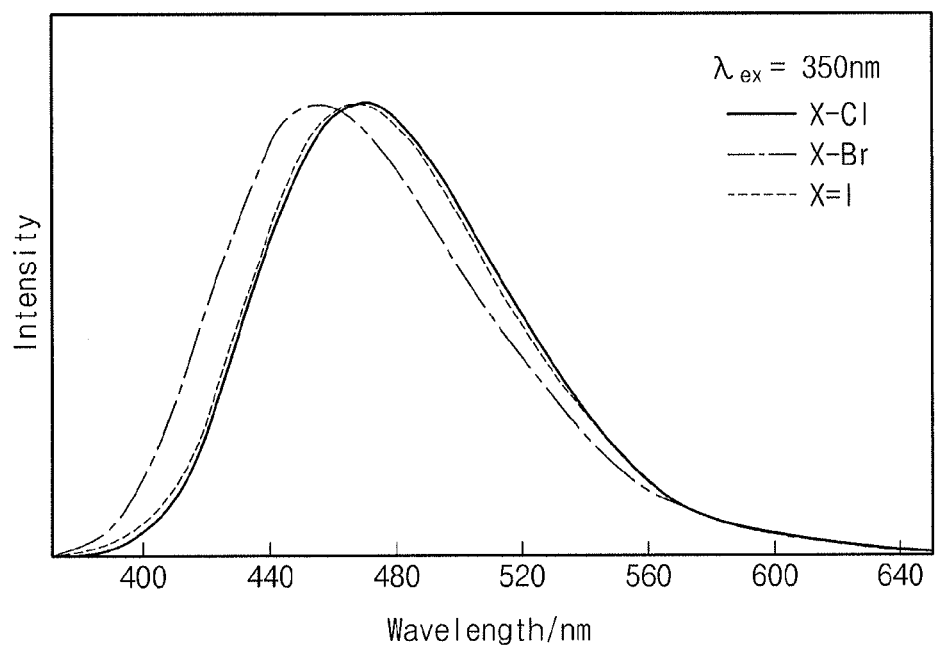
FIG. 3 illustrates a graph depicting emission spectra of copper(I) complexes [CuX(PPh$_3$)$_2$(4-Mepy)] (X=Cl$^-$, Br$^-$, I$^-$)

First, with respect to the copper(I) complexes [CuX(PPh₃)₂(4-Mepy)] (X=Cl⁻, Br⁻, I⁻) synthesized in Synthetic Examples 1 to 3, emission spectra were measured. The measuring of the emission spectrum was conducted by using an FR-6600 spectrofluorometer manufactured by JASCO Co. with respect to crystalline powders at room temperature. The wavelength of exciting light was 350 nm. The results are illustrated in FIG. 3. FIG. 3 illustrates a graph depicting emission spectra of the copper(I) complexes [CuX(PPh₃)₂(4-Mepy)] (X=Cl⁻, Br⁻, I⁻).

Referring to FIG. 3, all the copper(I) complexes [CuX(PPh₃)₂(4-Mepy)] (X=Cl⁻, Br⁻, I⁻) exhibited spectra without a similar vibration structure. [CuCl(PPh₃)₂(4-Mepy)] and [CuBr(PPh₃)₂(4-Mepy)] exhibited nearly the same emission maximum wavelength ($\lambda_{max}$=468 nm) and [CuI(PPh₃)₂(4-Mepy)] exhibited emission maximum wavelength ($\lambda_{max}$=455 nm), which is shifted to a shorter wavelength side.

After that, emission wavelength ($\lambda_{max}$) at the maximum, emission quantum yield ($\phi_{em}$), emission life ($\tau$) were measured at room temperature and 77K, respectively, and a radiation rate constant (kr) was computed with respect to the copper(I) complexes [CuX(PPh₃)₂(4-Mepy)] (X=Cl⁻, Br⁻, I⁻) synthesized in Synthetic Examples 1 to 3. The results are shown in the following Table 1.

The emission wavelength ($\lambda_{max}$) at the maximum was measured by using a FR-6600 spectrofluorometer manufactured by JASCO Co. as described above, and the emission quantum yield ($\phi_{em}$) was measured by using a C9920-02 absolute PL quantum yield measuring apparatus manufactured by Hamamatsu Photonics Co. In addition, the emission life ($\tau$) was measured by using C4334 streak camera manufactured by Hamamatsu Photonics Co. In addition, the radiation rate constant (kr) was computed by the formula $\phi_{em}/\tau$.

TABLE 1

|  | Temperature | $\lambda_{max}$[nm] | $\phi_{em}$ | $\tau$[μs] | kr[s⁻¹] |
| --- | --- | --- | --- | --- | --- |
| [CuCl(PPh₃)₂(4-Mepy)] | 298K | 468 | 0.99 | 10 | 1.1 × 10⁵ |
|  | 77K | 488 | 0.82 | 38 | 2.4 × 10⁴ |
| [CuBr(PPh₃)₂(4-Mepy)] | 298K | 467 | 0.95 | 15 | 7.4 × 10⁴ |
|  | 77K | 477 | 0.95 | 40 | 2.0 × 10⁴ |
| [CuI(PPh₃)₂(4-Mepy)] | 298K | 455 | 0.66 | 11 | 9.0 × 10⁴ |
|  | 77K | 458 | 0.76 | 52 | 1.4 × 10⁴ |

As shown in Table 1, the radiation rate constant (kr) is greater by about 4 to 20 times at room temperature (298K) when compared to that at 77K for all copper(I) complexes. From this results, it may be suggested that the emission process of the copper(I) complexes [CuX(PPh₃)₂(4-Mepy)] (X=Cl⁻, Br⁻, I⁻) is different at room temperature (298K) and 77K.

Figure 4:
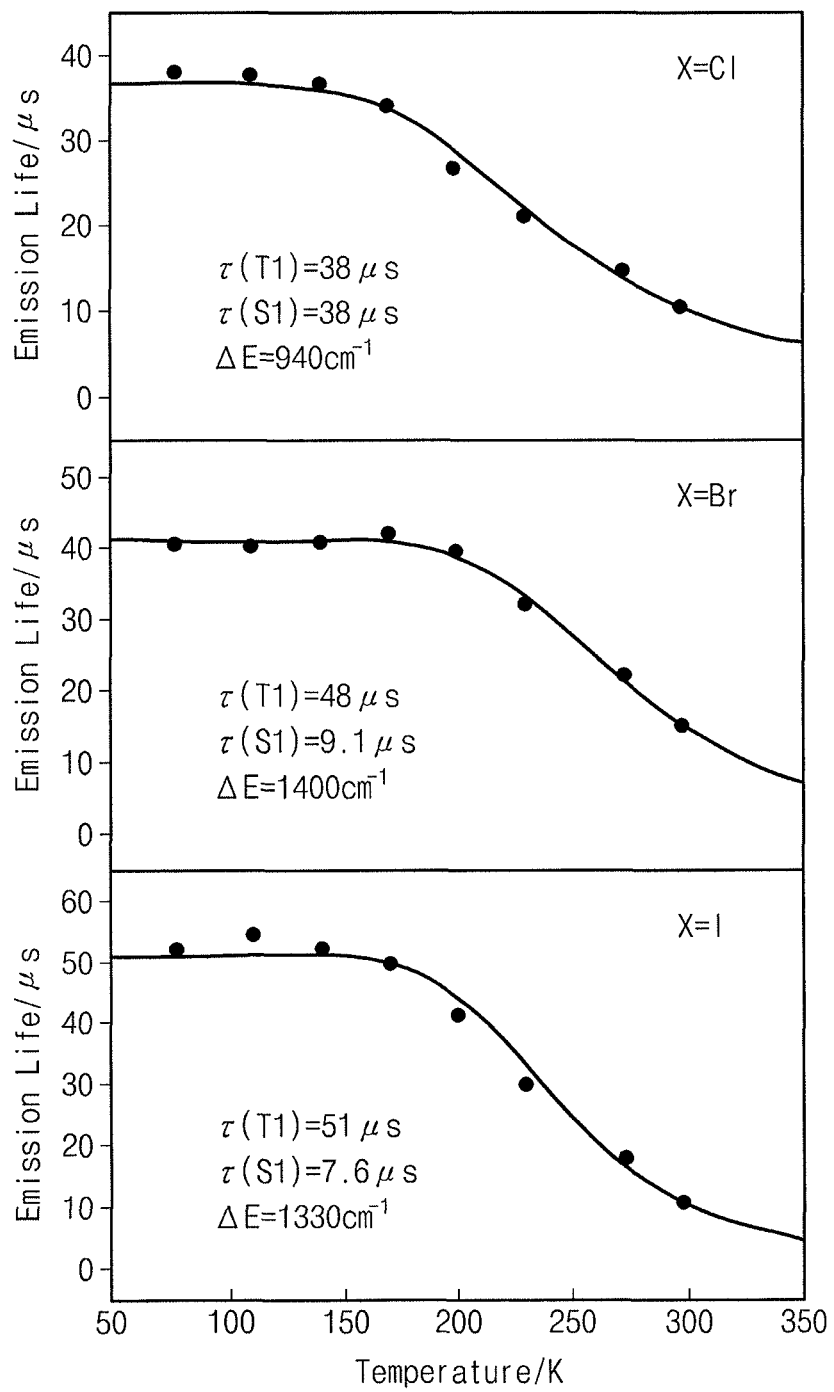
FIG. 4 illustrates a graph obtained by plotting the emission life of copper(I) complexes [CuX(PPh$_3$)$_2$(4-Mepy)] (X=Cl$^-$, Br$^-$, I$^-$) with respect to the temperature.

For the interpretation of the emission process of the copper (I) complexes [CuX(PPh₃)₂(4-Mepy)] (X=Cl⁻, Br⁻, I⁻) in more detail, emission life was measured for each temperature, and the temperature dependency of the emission life was interpreted. In addition, for the measurement of the emission life, the C4334 streak camera manufactured by Hamamatsu Photonics Co. described above was used. The results are illustrated in FIG. 4. FIG. 4 is a graph obtained by plotting emission life at each temperature for the copper(I) complexes [CuX(PPh₃)₂(4-Mepy)] (X=Cl⁻, Br⁻, I⁻).

As shown in FIG. 4, it may be found that the emission life was increased from room temperature (298K) to a lower temperature for all copper(I) complexes, and reached a steady value at about 150-160K.

The attenuation of the emission may be considered as being generated with single exponential. The temperature dependency shown in FIG. 4 may be considered as being generated by the emission from two states in thermal equilibrium. Simulation interpretation based on the following Equation 1 was conducted. In addition, in this simulation interpretation, the state with higher energy was set to the emission process of fluorescence, and the state with lower energy was set to the emission process of phosphorescence. The energy difference therebetween was set to ΔE.

$$k_{obs} = \frac{k_{T1} + k_{S1}K}{1 + K} \quad \text{[Equation 1]}$$

In the above Equation 1, $K_{obs}$ is a computed radiation rate constant according to the measured results, $K_{S1}$ is a radiation rate constant of only fluorescence, $K_{T1}$ is a radiation rate constant of only phosphorescence, K is a constant represented by the following Equation 2.

$$K = \frac{g_H}{g_L}\exp(-\Delta E/RT) \quad \text{[Equation 2]}$$

In the above Equation 2, $g_H$ and $g_L$ are the multiplicity for each state. In this simulation interpretation, since the state with higher energy was set to the emission process of the fluorescence, and the state with lower energy was set to the emission process of the phosphorescence, $g_H$ is 1, and $g_L$ is 3. In addition, R is the gas constant, and T is the absolute temperature.

By overlapping a fitting curve by the above interpretation with FIG. 4, the coincidence with the measured results may be found. The $K_{S1}$, $K_{T1}$ and $\Delta E$ values of the copper(I) complex according to an embodiment, computed by the above Equation 1 and the simulation interpretation are shown in the following Table 2. In Table 2, the $K_{S1}$, $K_{T1}$ and $\Delta E$ values of a known complex [Cu(pop)(NN)] with delayed fluorescence are shown together. Here, "pop" represents bis(2-(diphenylphosphanyl)phenyl)ether and "NN" represents bis(pyraxol-1-yl)borohydrate.

TABLE 2

| | $\Delta E[cm^{-1}]$ | $K_{S1}[s^{-1}]$ | $K_{T1}[s^{-1}]$ |
|---|---|---|---|
| [CuCl(PPh$_3$)$_2$(4-Mepy)] | 940 | 2.1 × 10$^7$ | 2.9 × 10$^4$ |
| [CuBr(PPh$_3$)$_2$(4-Mepy)] | 1070 | 2.4 × 10$^7$ | 2.0 × 10$^4$ |
| [CuI(PPh$_3$)$_2$(4-Mepy)] | 1070 | 7.1 × 10$^7$ | 2.0 × 10$^4$ |
| [Cu(pop)(NN)] | 800-1300 | 3.3 × 10$^7$ | 1.0 × 10$^4$-1.0 × 10$^5$ |

As shown from the above Table 2, the $K_{S1}$ value of the copper(I) complex according to embodiments was 2.1×10$^7$ to 7.1×10$^7$s$^{-1}$, and the $K_{T1}$ value thereof was 2.0×10$^4$ to 2.9×10$^4$ s$^{-1}$. Thus, it may be found that the $K_{S1}$ value of the copper(I) complex according to embodiments (2.1×10$^7$–7.1× 10$^7$s$^{-1}$) is the same as the $K_{S1}$ value of the known complex [Cu(pop)(NN)] with delayed fluorescence (3.3×10$^7$s$^{-1}$). In addition, with respect to the $K_{T1}$ value, the $K_{T1}$ value of the copper(I) complex according to embodiments (2.0×10$^4$–2.9× 10$^4$ s$^{-1}$) was the same as the $K_{T1}$ value of the known complex [Cu(pop)(NN)] with delayed fluorescence (1.0×10$^4$–1.0×10$^5$s$^{-1}$. With respect to $\Delta E$, $\Delta E$ of the copper(I) complex according to an embodiment (940-1070 cm$^{-1}$) was the same as $\Delta E$ of the known complex [Cu(pop)(NN)] with delayed fluorescence (800-1300 cm$^{-1}$). Accordingly, since all parameters of the copper(I) complex according to embodiments were found to be about the same as those of the known material with delayed fluorescence, the copper(I) complex may be judged to have delayed fluorescence of a thermal activation type.

Manufacture of Organic EL Device

To verify the effects of the copper(I) complex according to an embodiment, an organic EL device was manufactured by the following process.

Example 1

First, with respect to an ITO-glass substrate (manufactured by Sanyo Vacuum Industries) patterned and washed in advance, a surface treatment using ozone was performed. On the glass substrate, the thickness of the ITO layer was about 150 nm. Immediately after the ozone treatment, a layer including poly(3,4-ethylenedioxythiophene):poly(styrene-4-sulfonate) (PEDOT:PSS, Clevios PCH 8000 produced by Heraeus Co.) as a hole injection material was formed by a spin coat method on the ITO layer to a thickness of about 40 nm, and baking was performed at about 110° C. for about 1 hour.

Then, a layer including a light emitting ink obtained by dissolving 2-(4-biphenylyl)-5-(4-tert-butylphenyl)-1,3,4-oxadiazol (OXD-7) as an electron transport material, the copper(I) complex synthesized in Synthetic Example 1 as a luminescent material, and PVCz as a hole transport host material dissolved in dehydrated toluene (produced by Wako Pure Chemical Industries, Ltd.) was formed by a spin coat method to a layer thickness of about 100 nm, and baking was performed at about 80° C. for about 1 hour. In the light emitting ink, the mixing ratio of each material was OXD-7:copper(I) complex:PVCz=2.0:0.5:1.0 by weight.

Then, LiF was deposited as an electron injection material by a vacuum deposition method to a layer thickness of about 1.0 nm, and a layer was formed using Al to a thickness of about 250 nm as a cathode to manufacture an organic EL device 200. The organic EL device 200 thus manufactured was encapsulated together with a desiccant in a cavity glass using a UV-curable resin.

Examples 2 to 9

Organic EL devices 200 were manufactured by performing the same procedure described in Example 1 except for using the copper(I) complexes synthesized in Synthetic Examples 2 to 9 instead of the copper(I) complex synthesized in Synthetic Example 1 and used in Example 1.

Comparative Example 1

Organic EL devices 200 were manufactured by performing the same procedure described in Example 1 except for using [CuCl(PPh$_3$)$_3$] instead of the copper(I) complex synthesized in Synthetic Example 1 and used in Example 1. [CuCl(PPh$_3$)$_3$] differs from the copper(I) complex according to embodiments by including an additional PPh$_3$ instead of the ligand (L).

Figure 5:
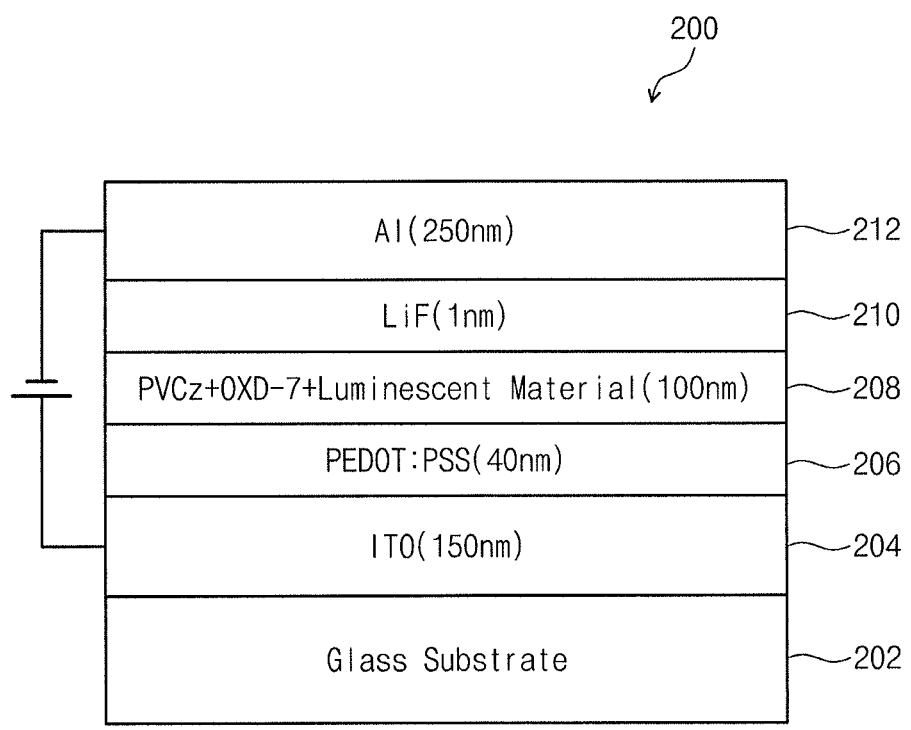
FIG. 5 illustrates a schematic diagram of an organic EL device manufactured using a luminescent material according to an embodiment.

The schematic diagram of the organic EL device 200 according to Examples 1 to 9 and Comparative Example 1 is shown in FIG. 5. The organic EL device 200 thus manufactured includes a substrate 202, an anode 204 disposed on the substrate 202, a hole injection layer 206 disposed on the anode 204, an emission layer 208 disposed on the hole injection layer 206, an electron injection layer 210 disposed on the emission layer 208 and a cathode 212 disposed on the electron injection layer 210.

Evaluation Results

The evaluation results of the organic EL devices 200 manufactured in Examples 1 to 9 and Comparative Example 1 are illustrated in the following Table 3. In addition, for the evaluation of the electroluminescent properties of the organic EL devices 200 thus manufactured, a C9920-11 brightness light distribution characteristics measurement system manufactured by Hamamatsu Photonics Co. was used. In the following Table 3, emission efficiency was measured at current density of 20 mA/cm$^2$.

In Table 3, "4-Mepy" represents 4-methylpyridine (Formula (15)), "iq" represents i-quinoline (Formula (3)), and "1,6-nap" represents 1,6-naphthyridine (Formula (10)).

TABLE 3

|  | Example 1 | Example 2 | Example 3 | Example 4 | Example 5 | Example 6 | Example 7 | Example 8 | Example 9 | Comparative Example 1 |
|---|---|---|---|---|---|---|---|---|---|---|
| ligand L | 4-Mepy | 4-Mepy | 4-Mepy | iq | iq | iq | 1,6-nap | 1,6-nap | 1,6-nap | PPh3 |
| ligand X | Cl | Br | I | Cl | Br | I | Cl | Br | I | Cl |
| Emission efficiency [cd/A.] | 2.1 | 1.8 | 1.7 | 2 | 1.3 | 1.6 | 0.5 | 1.4 | 1.9 | 0.2 |

As shown in the above Table 3, the organic EL devices of Examples 1 to 9 according to exemplary embodiments exhibited higher emission efficiency when compared to that of the organic EL device of Comparative Example 1.

In addition, even though exemplary embodiments of the organic EL devices using the copper(I) complexes according to exemplary embodiments as luminescent materials were explained, it is to be understood that, the luminescent material including the copper(I) complex according to embodiments may be used in other luminescent devices or luminescent apparatuses. As examples, the organic EL devices shown in FIGS. 1 and 5 may be used in an organic EL device of a passive-matrix driving type, or in an organic EL device of an active-matrix driving type.

By way of summation and review, embodiments provide a novel and improved material for an organic EL device of which emission efficiency may be improved, and an organic EL device Example embodiments have been disclosed herein, and although specific terms are employed, they are used and are to be interpreted in a generic and descriptive sense only and not for purpose of limitation. Accordingly, it will be understood by those of skill in the art that various changes in form and details may be made without departing from the spirit and scope thereof as set forth in the following claims.

What is claimed is:

1. A material for an organic electroluminescent (EL) device, the material comprising a copper(I) complex represented by the following Formula 1:

[CuX(PPh₃)₂L]   [Formula 1]

in the above Formula 1,
X is an anion,
PPh₃ is triphenylphosphine, and
L is a ligand represented by one of the following ligands (4) to (14) and (18) to (22):

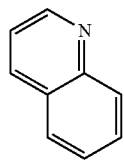
(4)

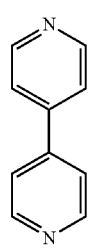
(5)

-continued

(6)

(7)

(8)

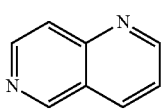
(9)

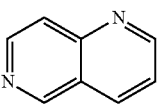
(10)

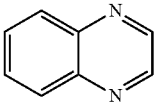
(11)

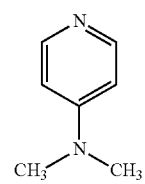
(12)

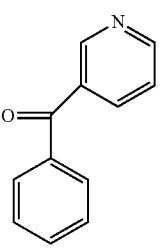
(13)

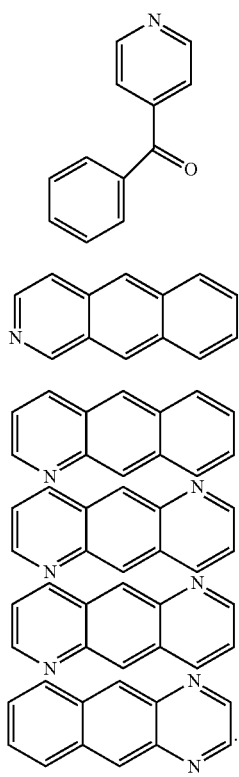

(14)

(18)

(19)

(20)

(21)

(22)

2. The material for an organic EL device as claimed in claim 1, wherein the copper(I) complex exhibits delayed fluorescence.

3. The material for an organic EL device as claimed in claim 1, wherein the nitrogen-containing heterocyclic ligand is 1,6-naphthyridine.

4. The material for an organic EL device as claimed in claim 3, wherein X is an anion selected from the group of a halide ion, a nitrate ion, and a perchlorate ion.

5. The material for an organic EL device as claimed in claim 4, wherein X is one of Cl$^-$, Br$^-$ and I$^-$.

6. The material for an organic EL device as claimed in claim 1, wherein the copper(I) complex is a compound represented by the following Formula (1C):

Formula (1C)

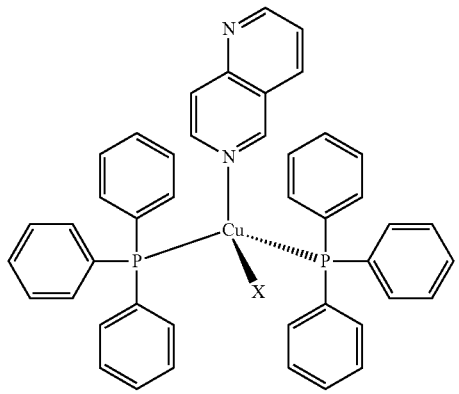

in the above Formula 1C, X is one of Cl$^-$, Br$^-$ and I$^-$.

7. An organic electroluminescent (EL) device, comprising a copper(I) complex represented by the following Formula 1:

[CuX(PPh$_3$)$_2$L]    [Formula 1]

in the above Formula 1,

X is an anion,

PPh$_3$ is triphenylphosphine, and

L is a ligand represented by one of the following ligands (4) to (14) and (18) to (22):

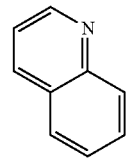

(4)

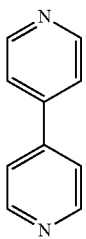

(5)

(6)

(7)

(8)

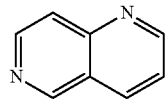

(9)

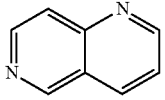

(10)

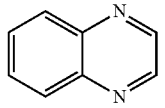

(11)

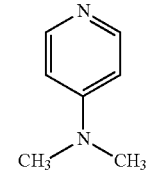

(12)

(13) 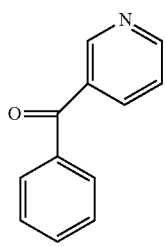

(14) 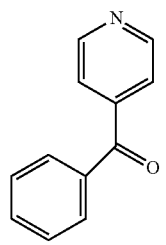

(18) 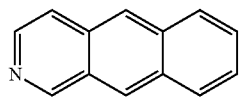

(19) 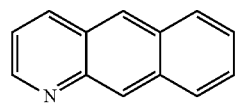

(20) 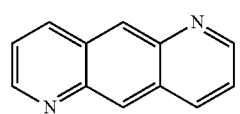

(21) 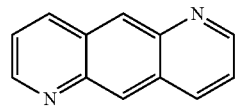

(22) 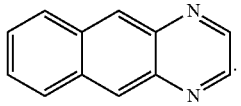

8. The organic EL device as claimed in claim 7, wherein the copper(I) complex exhibits delayed fluorescence.

9. The organic EL device as claimed in claim 7, wherein the nitrogen-containing heterocyclic ligand is 1,6-naphthyridine.

10. The organic EL device as claimed in claim 9, wherein X is an anion selected from the group of a halide ion, a nitrate ion, and a perchlorate ion.

11. The organic EL device as claimed in claim 10, wherein X is one of Cl⁻, Br⁻ and I⁻.

12. The organic EL device as claimed in claim 7, wherein the copper(I) complex is a compound represented by the following Formula (1C):

Formula (1C)

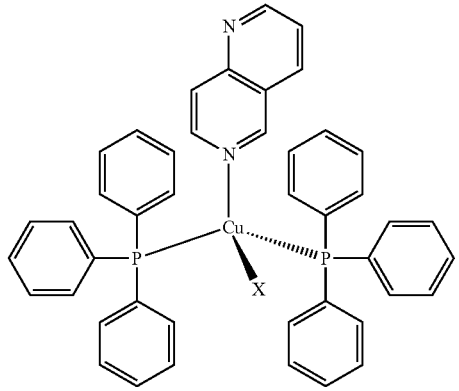

in the above Formulae (1A) to (1C), X is one of Cl⁻, Br⁻ and I⁻.

* * * * *